(12) United States Patent
Spivack et al.

(10) Patent No.: US 7,851,154 B2
(45) Date of Patent: Dec. 14, 2010

(54) GC TAG-MODIFIED BISULFITE GENOMIC DNA SEQUENCING FOR CONTINUOUS METHYLATION SPECTRA

(76) Inventors: Simon Daniel Spivack, 258 Hanley Rd., Nassau, NY (US) 12123; James Gordon Herman, 206 Dunbeath Ct., Lutherville, MD (US) 21093; Weiguo Han, 19C Lewis Ave., Menands, NY (US) 12204

( * ) Notice: Subject to any disclaimer, the term of this patent is extended or adjusted under 35 U.S.C. 154(b) by 385 days.

(21) Appl. No.: 11/492,288

(22) Filed: Jul. 24, 2006

(65) Prior Publication Data

US 2007/0054295 A1 Mar. 8, 2007

Related U.S. Application Data

(60) Provisional application No. 60/701,923, filed on Jul. 22, 2005.

(51) Int. Cl.
*C12Q 1/68* (2006.01)
*C12P 19/34* (2006.01)

(52) U.S. Cl. ......................... 435/6; 435/91.2

(58) Field of Classification Search .................. 435/6, 435/91.2
See application file for complete search history.

(56) References Cited

U.S. PATENT DOCUMENTS 7,252,935 B2 * 8/2007 Sidransky .................... 435/6
2004/0002071 A1 * 1/2004 Ralph et al. .................. 435/6

OTHER PUBLICATIONS

Herman et al. Proc. Natl. Acad. Sci. USA, 1996, vol. 93, p. 9821-9826.*
Yanagawa et al. Cancer Sci., 2003, vol. 94(7), p. 589-592.*
Grunau, et al., "Bisulfite genomic sequencing: systematic investigation of critical experimental parameters", Nucleic Acids Research, vol. 29, No. 13, pp. 1-7, 2001.
Russo, et al., "Differential DNA Hypermethylation of Critical Genes Mediates the Stage-Specific Tobacco Smoke-Induced Neoplastic Progression of Lung Cancer", Clin. Cancer Research, 2005, 11(7), pp. 2466-2470, Apr. 1, 2005.
Belinsky, et al., "Promoter Hypermethylation of Multiple Genes in Sputum Precedes Lung Cancer Incidence in a High-Risk Cohort", Cancer Res. 2006, 66: (6), pp. 3338-3344, Mar. 15, 2006.
Esteller, Manel, "The necessity of a human epigenome project", Carcinogensis, vol. 27, No. 6, pp. 1121-1125, May 13, 2006.
Harden, et al., "Gene Promoter Hypermethylation in Tumors and Lymph Nodes of Stage I Lung Cancer Patients", Clinical Cancer Research, vol. 9, pp. 1370-1375, Apr. 2003.
Zöchbauer-Müller, et al., "Aberrant Promoter Methylation of Multiple Genes in Non-Small Cell Lung Cancers", Cancer Research 61, pp. 249-255, Jan. 1, 2001.
Sanchez-Cespedes, et. al., "Gene Promoter Hypermethylation in Tumors and Serum of Head and Neck Cancer Patients", Cancer Research, 60, pp. 892-895, Feb. 15, 2000.
Herman, et al., "Gene Silencing in Cancer in Association with Promoter Hypermethylation", N. Engl. L. Med., 329; 21, pp. 2042-2054, Nov. 20, 2003.
Belinsky, Steven A., "Gene-Promoter Hypermethylation as a Biomarker in Lung Cancer", Nature Reviews/Cancer, vol. 4, pp. 707-717, Sep. 2004.
Klose, et al., "Genomic DNA methylation: the mark and its mediators", Trends in Biochemical Sciences, vol. 31, No. 2, pp. 89-97, Feb. 2006.
Jones, et al., "The Role of DNA Methylation in Mammalian Epigenetics", Science (Epigenetics Viewpoint), vol. 293, pp. 1068-1070, Aug. 10, 2001.

* cited by examiner

*Primary Examiner*—Kenneth R. Horlick
*Assistant Examiner*—Joyce Tung
(74) *Attorney, Agent, or Firm*—Heslin Rothenberg Farley & Mesiti P.C.; Kathy Smith Dias

(57) ABSTRACT

The present invention relates to a tag-modified bisulfite genomic sequencing (tBGS) method developed for simplified evaluation of DNA methylation sites. The method employs direct cycle sequencing of PCR products at kilobase scale, without conventional DNA fragment cloning. The method entails subjecting bisulfite-modified genomic DNA to a second-round PCR amplification employing GC-tagged primers. The invention also relates to a method for identifying a patient at risk for lung cancer using the tBGS technique disclosed.

19 Claims, 9 Drawing Sheets

CYP1B1 Promoter

GSTP1 Promoter:

☐ Unmethylated CpG
▦ 10~30% methylated CpG
▨ 30~60% methylated CpG
▮ 60~90% methylated CpG
■ 100% Methylated CpG

GC TAG-MODIFIED BISULFITE GENOMIC DNA SEQUENCING FOR CONTINUOUS METHYLATION SPECTRA

CROSS-REFERENCE TO RELATED APPLICATIONS

This application is a non-provisional of and claims the benefit of U.S. Provisional Application No. 60/701,923, filed Jul. 22, 2005, the entire disclosure of which is incorporated by reference in its entirety in the present application.

STATEMENT OF RIGHTS UNDER FEDERALLY-SPONSORED RESEARCH

This invention was made with U.S. Government support under Grant Nos. NIH/NCI/R21-CA94714; NIH/NC1/RO1-CA 106186. The U.S. Government has certain rights in this invention.

FIELD OF THE INVENTION

The invention relates generally to a method for determining the degree of genomic DNA. The invention, therefore, provides a method for identifying an individual at risk for a disease such as lung cancer characterized by transcriptional inactivation of tumor suppressor genes.

BACKGROUND OF THE INVENTION

Methylation of cytosines located 5' adjacent to guanosine is known to have a repressive effect on the expression of many eukaryotic genes (1-6).

Aberrant methylation of normally unmethylated CpG islands has been documented as a relatively frequent event in experimentally immortalized and transformed cells, and it has been clearly associated with transcriptional inactivation of defined tumor suppresser genes in human cancers (7, 8). Hundreds of CpG islands are now known to exhibit the characteristic of hypermethylation in tumor cells (9). Therefore, mapping of methylation patterns in CpG islands has become important for understanding both normal and pathologic gene expression events.

The most direct mechanism by which DNA methylation can interfere with transcription is to prevent the binding of basal transcriptional machinery or ubiquitous transcription factors that require contact with cytosine in the major groove of the double helix. Most mammaliam transcription factors have GC-rich binding sites and many have CpGs in their DNA recognition elements. Binding by several of these factors is impeded or abolished by methylation of CpG.

The highest density of nonmethylated CpGs in the vertebrate genome is found in CpG islands, which usually contain promoter or other regulatory DNA that is required for active transcription of a gene. CpG island chromatin is enriched in hyperacetylated histones and deficient in linker histones. These are important features of transcriptionally competent chromatin templates. In contrast, chromatin assembled on artificially methylated DNA becomes associated with hypoacetylated histones, refractory to nuclease or restriction endonuclease digestion and transcriptionally silent. Many tumor-suppressor and other cancer-related genes have been found to be hypermethylated in human cancer cells (48).

The different classes of genes that are silenced by DNA methyaltion include tumor-suppressor genes, genes that suppress tumor invasion, and metastasis; DNA repair genes; genes for hormone receptors; and genes that inhibit angiogenesis. Gene silencing by hypermethylation of genes has been recognized as an important mechanism of carcinogenesis that has great promise for cancer prevention and therapy. A first step is the identification of such genes or regulatory elements. The first described alteration in the retinoid pathway was the leukemogenic role of the PML-RAR fusion protein. Evidence has since been obtained that supports the role of RARβ2 as a tumor-suppressor gene, including the role in the induction of RARβ2 related to the chemopreventive effects of retinoids, the loss of RARβ2 expression in human neoplasms. Frequent chromosomal losses at 3P21-3p24 where RARβ2 is located, and the mehtylation-mediated silencing of RARβ2. The silencing of the cellular retinoid-binding protein-1 gene (CRBP1) was reported as a common alteration in human cancer (48).

The cytochromes P450 are important phase I bioactivating carcinogen metabolism enzymes, and have been hypothesized to be responsible, in part, for inter-individual differences in susceptibility to chemically-induced disease (10-15); CYP1B1 is among the most highly expressed P450 enzyme in human lung and human breast, and it bioactivates both polyaromatic hydrocarbons and estradiol to highly mutagenic species.

Glutathione-S-transferases (GSTs) are phase II deactivating enzymes critically involved in DNA protection from electrophilic metabolites of carcinogens and reactive oxygen, nitrogen, lipid species, and chemotherapeutic agents. GSTP1 is the most highly expressed GST in the human lung and upper airway (16,17). Observational studies on normal tissue expression patterns for both CYP1B1 and GSTP1 gene products suggest inter-individual variation over several orders of magnitude, not explained by measured environmental exposures (16-18). Variation in regulatory-region features, including promoter genetic polymorphisms, transcription factor levels, and epigenetic features are hypothesized to vary across individuals. To our knowledge, no detailed survey of variation in normal tissue epigenetic features has been performed across kilobase-level expanses of promoter DNA sequence to explain this inter-individual and inter-tissue variation.

Several methods have been developed to determine the methylation status of cytosines in DNA (19). These include digestion with methylation-sensitive restriction enzymes, as in restriction landmark genomic scanning (20), oligonucleotide arrays (21), pyrosequencing (22) or MS-based primer extension-based methods (23), as well as bisulfite genomic DNA sequencing (BGS) and methylation-specific PCR (MSP). MSP is now an established technology for the monitoring of abnormal gene methylation in selected gene sequences (24). MSP is a discontinuous method for assaying DNA sequence; it generally samples oligomer annealing sites of approximately 20 bases in and around known methylation CpG sites. The technique relies on bisulfite chemical treatment of genomic DNA, to chemically convert unmethylated cytosines to uracils, and the replacement of uracil, in the subsequent PCR, with thymidines. The careful design of MSP primers allows, in separate uniplex reactions, either a match or a mismatch at the CpG site in question, and therefore either a successful or unsuccessful PCR, with a categorical readout; either positive or negative. Both qualitative and quantitative MSP (25-29) require prior genomic methylation screening, to direct primer design to appropriate specific target sequence for analysis. MALDI-TOF mass spectrometry has recently been reported as an alternative genome-wide methylation mapping approach (30), but may be resource intensive from a procedural, instrumentation, and informatics perspective.

BGS offers a continuous readout of the entire, detailed, base-by-base methylation map of a genomic DNA sequence (31, 32). The technique also relies on initial bisulfite modification of DNA, and as a final step, direct cycle sequencing of the resulting PCR-amplified sequence. PCR primers are designed external to potential methylation sites. However, because of the bisulfite conversion of unmethylated C=>U in the template, there is a paucity of C (sense) or G (antisense) strand nucleotides in the PCR product. Thus, there is a skewed (low) GC content, and direct cycle sequencing results in artefactual background signal attributable to excess unused dCIP and dGTP in the sequencing reaction.

Conventional bisulfite sequencing commonly requires the cloning of PCR product for two reasons: First, the incorporation into the plasmid vector allows skewed GC content to be compensated for by the external plasmid sequence. Second, this approach provides precise methylation patterns of individual DNA molecules, overcoming tissue heterogeneity issues affecting methylation patterns at individual CpG sites. However, this requirement makes conventional BGS time consuming and labor intensive, and it precludes large-scale surveillance studies across multiple regions, genes, tissues, and donors.

SUMMARY OF THE INVENTION

The present invention relates to a novel method where the degree of DNA methylation is determined using tag-modified bisulfite genomic sequencing (tBGS) and avoids the need for cloning of the PCR product entirely. The invention provides a method for identifying an individual at risk for a disease, for example, cancer, characterized by transcriptional deactivation of tumor suppressor genes.

In one aspect, the invention relates to a method for determining the degree of methylation of genomic DNA, said method comprising:

(a) providing a genomic DNA;
(b) modifying said DNA by bisulfite conversion of cytosine to uracil;
(c) amplifying said bisulfite-modified DNA by PCR to produce a first PCR product;
(d) amplifying said first PCR product by PCR using a tag-modified primer to yield a second PCR product comprising a cytosine/guanosine enriched tag, wherein said tag-modified primer comprises a tag having a nucleotide sequence enriched for cytosine or guanosine;
(e) purifying said second PCR product;
(f) sequencing said purified second PCR product using a sequencing primer targeted to the cytosine/guanosine enriched tag of said second PCR product to obtain a nucleotide sequence of said second PCR product;
(g) analyzing the nucleotide sequence obtained from step (f) to determine the degree of methylation of said DNA.

In a related aspect, the invention provides a method for identifying an individual at risk for lung cancer comprising:

(a) providing a DNA sample from said patient;
(b) modifying said DNA by bisulfite conversion of cytosine to uracil;
(c) amplifying said bisulfite-modified DNA by PCR to produce a first PCR product;
(d) amplifying said first PCR product by PCR using a tag-modified primer to yield a second PCR product comprising a cytosine/guanosine enriched tag, wherein said tag-modified primer comprises a tag having a nucleotide sequence enriched for cytosine or guanosine;
(e) purifying said second PCR product;
(f) sequencing said purified second PCR product using a sequencing primer targeted to the cytosine/guanosine enriched tag of said second PCR product to obtain a nucleotide sequence of said second PCR product;
(g) analyzing the nucleotide sequence obtained from step (f) to determine the degree of methylation of said DNA from said patient, wherein a high degree of methylation is indicative of a risk of lung cancer.

DETAILED DESCRIPTION OF THE INVENTION

Figure 1:
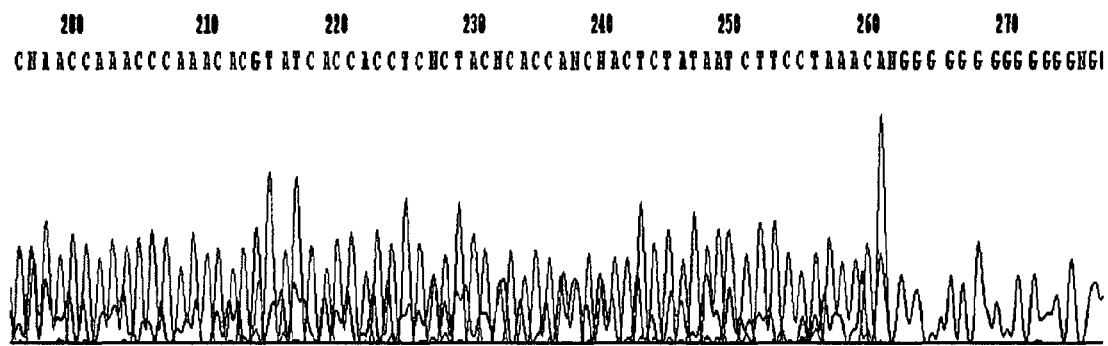
FIG. 1 is a chromatogram tracing of direct sequencing of the bisulfite-modified DNA-PCR product for CYP1B1 gene promoter using standard-design PCR primers in the absence of cloning(SEQ ID NO: 56).

All patents, published applications and other references cited herein are incorporated by reference in their entirety into the present application.

In practicing the present invention, many conventional techniques in molecular biology, microbiology, and recombinant DNA are used. Such techniques are well known and are explained in, for example, Sambrook et al., 1984, *Molecular Cloning: A Laboratory Manual*, Second Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984 (M. L. Gait ed.); Nucleic Acid Hybridization, 1985, (Hames and Higgins, eds.); *Transcription and Translation*, 1984 (Hames and Higgins, eds.); *Animal Cell Culture*, 1986 (R. I. Freshney ed.); *Immobilized Cells and Enzymes*, 1986, (IRL Press); Perbas, 1984, *A Practical Guide to Molecular Cloning;* the series, *Methods in Enzymology* (Academic Press, Inc.); *Gene Transfer Vectors for Mammalian Cells*, 1987 (J. H. Miller and M. P. Calos eds., Cold Spring Harbor Laboratory); and *Methods in Enzymology* Vol. 154 and Vol. 155 (Wu and Grossman, and Wu, eds., respectively); *Current Protocols in Molecular Biology*, John Wiley & Sons, Inc. (1994), and all more recent editions of these publications.

The methods disclosed in this application can be applied to any tissue or DNA sequence and can aid in identifying a patient at risk for cancer, including lung cancer and breast cancer, and various other cancers, diseases or disorders characterized by hypermethylation of DNA, including inflammatory disease.

It should be noted that although the examples provide a method wherein bisulfite modified genomic DNA undergoes amplification by two rounds of PCR, the disclosed invention can be performed by a single PCR amplification. Also, multiple primer sets can be used.

Definitions:

The term "tag-modified primer" refers to a DNA primer containing a GC tag added to either the 5' or 3' end of a DNA strand, rich in cytosine if a forward primer, and rich in guanosine if a reverse primer, selected to be complementary to the analytically-relevant sequence. Table 2 provides examples of tag-modified primers for CYP1B1 and GSTP 1 promoters.

The term "primer targeted to the GC tag" refers to a DNA primer that will bind to the GC tag of the tag-modified primer.

The term tag refers to a base(s) attached to or incorporated into DNA and used to detect the presence of a specific DNA sequence.

EXAMPLES

Examples presented in this application show the utility of tBGS in the mapping of methylation patterns, in the promoters of two carcinogen-metabolizing genes, across human tissue types and cells, including exfoliated and exhaled specimens, and across individual subjects.

Examples of some of the embodiments intended to be encompassed by the instance invention are provided. The examples given are meant to be illustrative, and are in no way intended to be limiting to the particular invention.

The disclosed strategy was applied to over 40 samples of human genomic DNA for approximately 2.0 kb promoter sequence for two genes, CYP1B1 and GSTP1, each requiring multiple (5-8) fragments for separate amplification reactions, enabling the detailed comparison of promoter methylation specra across individual human subjects. A total of 46 Caucasian subjects were analyzed in the present study, under ongoing protocols approved by both the Albany Medical Center and the New York State Department of Health Institutional Review Boards. Informed consent was explicit, and privacy was protected by stripping of traceable identifiers from clinical samples. The group consisted of 18 current smokers, 22 former smokers, and six never-smokers; smoking status was confirmed by plasma nicotine and cotinine biomarkers, and by self-reported history (16, 17). Both peripheral blood mononuclear cell (PBMC) and mouthwash-exfoliated buccal cell samples were obtained from 40 individuals, of whom 27 had a new diagnosis of lung cancer (untreated), and 13 were non-cancer controls. For the 10 subjects donating lung tissue, pathologically-confirmed non-small cell lung tumor (n=9) or benign bronchial adenoma (n=1) tissue was paired with adjacent, histologically nontumor tissue; five of these 10 individuals were among the 40 providing both blood cells and buccal cells. One additional donor (never smoker) provided exhaled breath condensate. Subjects were interviewed and peripheral blood and mouthwash-exfoliated cells were collected pre-operatively, before any clinically-indicated diagnostic or therapeutic lung resectional surgery.

Peripheral Blood Mononuclear Cell and Buccal Cell Collection:

Phlebotomy was performed by standard clinical technique; isolation of PBMC was performed in standard fashion using a Ficoll gradient technique as described (33). Mouth-washed buccal cell specimens were obtained by having the subject rinsing the mouth thoroughly with 7.5 ml of a commercially-available, standard mouthwash (Scope®, Proctor & Gamble) for 10-15 sec, with deposition of the resulting rinse into a sterile container for storage at −80° C. until subsequent analysis. Blood and buccal specimens were collected during the same session, and within 24-48 hr of the relevant surgical lung biopsy and/or resection.

Exhaled Breath Condensate (EBC) Collection:

One subject volunteered to donate exhaled breath condensate (EBC), which was collected in an EcoScreen® exhaled breath condenser (Jaeger, Hoechberg, Germany) during quiet tidal volume breathing. Approximately 1.0 ml of EBC was collected in the condenser portion (<0° C.) of the device during 10 min of normal tidal breathing; this volume contained between 250-500 ng genomic DNA on replicate samples. The system offers virtually no resistance to tidal volume breathing. This collection procedure was repeated at two time points.

Cell Culture:

Normal human bronchial epithelial (NHBE) cells were primary, non-transformed, and non-immortal, and were obtained from a commercial source (BioWhittaker, Inc., Walkersville, Md.). NHBE cells were maintained in BEGM medium (BioWhittaker, Inc.) and cultured in BEGM medium, as previously described (29). A549 cells (lung adenocarcinoma cells) from ATCC were cultured in F12K nutrient mixture (Invitrogen) supplemented with 10% fetal bovine serum and 10 μg/ml gentamicin at 37° C. in a humidified 5% $CO_2$ atmosphere.

Preparation of Genomic DNA:

Any source of DNA is suitable. For example, monocucelar cells isolated in standard fashion using a Ficoll gradient technique is suitable. For boccal cells, a standard mouthwash procedure can be used. Genomic DNA was isolated using a standard isolation kit (Gentra Systems, Minneapolis, Minn.) according to the manufacturer's recommendations. Briefly, cell lysis, where applicable, was followed by RNase and proteinase K treatment, isopropanol precipitation, ethanol washing, and storage in a hydration solution at −20° C.

Bisulfite Modification:

Genomic DNA was modified by EZ DNA Methylation Kit (Zymo Research, Orange, Calif.). Briefly, 1 μg of DNA in a volume of 50 μl was denatured by 5 μl M-dilution Buffer for 15 min at 37° C. Bisulfite-containing CT-Conversion Reagent (100 μl) was added and mixed, and samples were incubated at 50° C. for 18 hr. Modified DNA was purified by Zymo-Spin 1 Column, and used immediately or stored at −20° C.

GC Tag-modified Bisulfite Genomic DNA Sequencing:

The sense strand of bisulfite-modified genomic DNA was amplified with primers specific for the CYP1B1 and GSTP1 promoters (Table 1). For the CYP1B1 promoter, PCR conditions were: 95° C. for 15 min, then 5 cycles of 95° C. for 10 sec, 54° C. for 30 sec, 72° C. for 1 min, and 35 cycles of 95° C. for 10 sec, 48° C. for 30 sec, 72° C. for 1 min, and finally 5 min at 72° C. For the GSTP1 promoter, conditions were: 95° C.; for 15 min, then 40 cycles of 95° C. for 30 sec, 50° C. for 30 sec, 72° C. for 1 min, and finally 7 min at 72 ° C. The PCR mixture contains 1×buffer (Qiagen, Valencia, Calif.) with 1.5 mM $MgCl_2$, 1 μM of each promoter-specific sense and anti-sense primer, and 5 U of HotStar® Taq polymerase (Qiagen) and 50-100 ng bisulfite-modified genomic DNA. The PCR thermal profiles were programmed into a Perkin-Elmer 9700 thermocycler. These first-round PCR products were then used as template (1 µl) and re-amplified by tagged primers (FIG. 2, Table 2).

Figure 2:
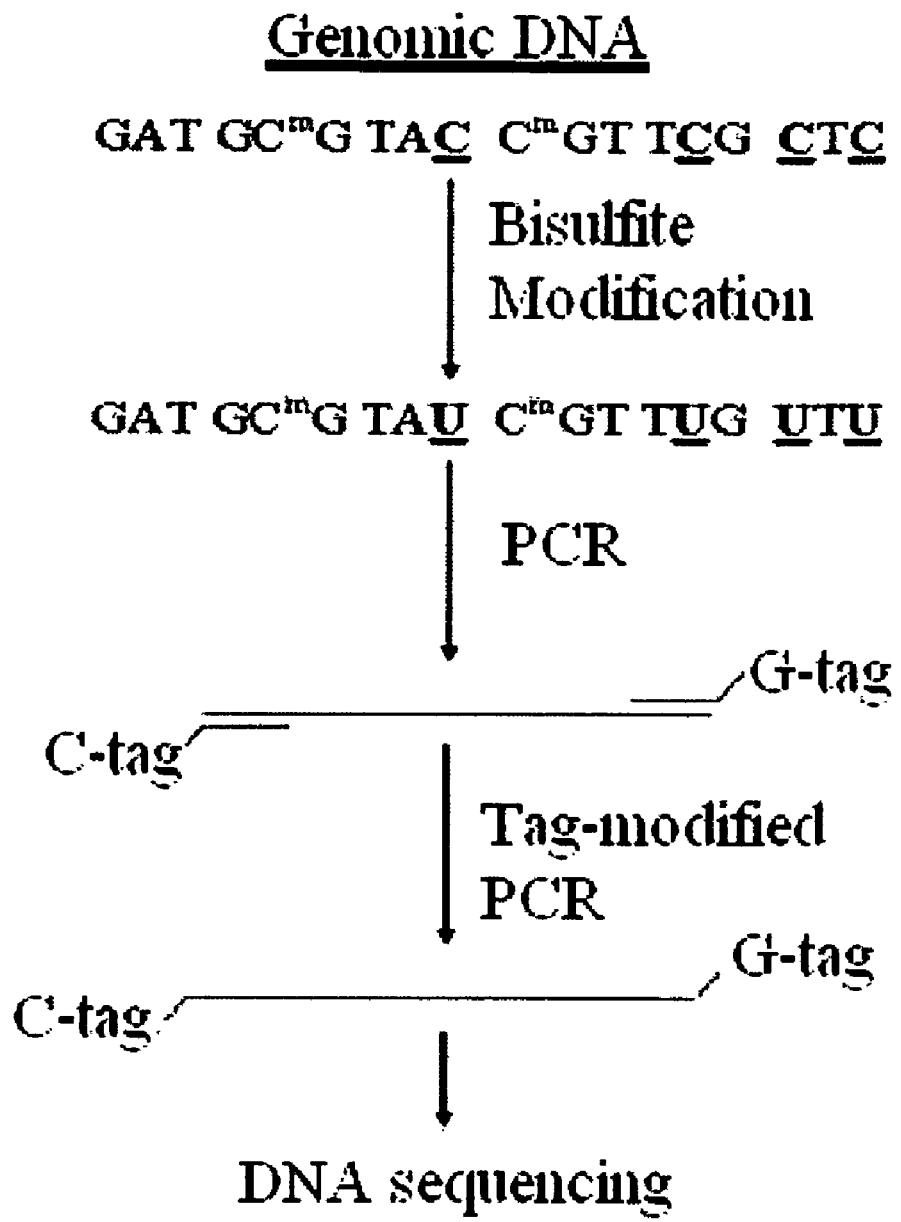
FIG. 2 is a flow chart depicting the strategy of the GC tag-modified bisulfite genomic sequencing approach (SEQ ID NOS 57 & 58, respectively in order of appearance).

FIG. 2 depicts the initial bisulfite conversion of genomic DNA amplified in a standard PCR reaction in the first round, and then C- or G-tagged primers are employed to alter the base composition of the second-round PCR product. Standard sequencing is then reliably performed [see USPTO patent pending #60/592337].

The second-round PCR conditions for CYP1B1 were: 95° C. for 15 min, and then 35 cycles of 95° C. for 10 sec, 55° C. for 20 sec, 72° C. for 20 sec, and finally 7 min at 72° C. The second-round PCR conditions for GSTP1 were: 95° C. for 15 min, then 40 cycles of 94° C. for 30 sec, 60° C. for 30 sec, 72° C. for 1 min, and finally 7 min at 72 ° C. PCR products were then purified with a Gel Extraction Kit (Qiagen) and subjected to direct-cycle sequencing on a Perkin-Elmer Biosystems ABI model 3100/3700 automated DNA sequencer, using tag-targeted sequencing primers: 5'-CCACTCACT-CACCCACCC-3' (SEQ ID NO: 1)(Forward); 5'-GGGTGG-GAGGTGGGAGGG-3' (SEQ ID NO: 2) (reverse). All samples were analyzed in duplicate, from bisulfite modification to sequencing. Manual review of sequence chromatograms containing two peaks at any one CpG locus was performed by measuring the peak height of the C (or anti-sense G) versus the combined height of the C+T peaks, and generating a C/C+T (or anti-sense A/A+G) peak height representing the methylated fraction of DNA molecules, as a percentage (34, 35).

Conventional Bisulfite Genomic Sequencing:

Methylation status was verified in one fragment of each of the two genes, by cloning the first-round PCR product from each, derived from the same sample of bisulfite treated genomic DNA, into PCR-2.1-TOPO vector (Invitrogen), and performing direct cycle sequencing on 10 clones per fragment.

Primer Design Principles for Successful tBGS:

Design principles for the first-round PCR primer are as follows. (1) CpG sites in the primer annealing site should be avoided. (2) If they are unavoidable, however, degenerate primers employing C/T for in the forward primer and G/A for G in the reverse primer can be employed. (3) Amplification of only one strand (e.g., the sense strand) of the bisulfite-treated genomic DNA (4) For any given strand, the forward primer should contain multiple T's, deriving from non-CpG site bisulfite-converted C's near the 3' end, so as to distinguish bisulfite-converted target strand from other (contaminating or incompletely converted) strands. The same principle (analogously using multiple A's) holds for the reverse primer. (5) Higher annealing temperatures (>50° C.) are better for specific amplification.

Design principles for the second-round PCR, using GC-tag modified primers, are as follows. (1) GC-tag length of 18-22 bases, containing at least 50% C (for forward primer) or G (for reverse primer), has proven successful; the upper limit of tag length has not yet been determined. (2) The sequence-specific region of the tagged oligo primer is most easily limited to approximately 15-20 bases, yielding a tagged primer<40-45 bp in length, which is compatible with standard oligomer synthesis purity constraints. (3) The PCR product length is usually limited to 200-300 bp, such that a 20-base tag at each end can enhance GC content of the PCR product to greater than 10-20%.

Verification by Conventional BGS:

Bisulfite-treated genomic DNA from single donor NHBE cells and single donor A549 cells was PCR amplified for both CYP1B1 and GSTP1 promoters, using primers 1B1MF1B, 1B1MR4 and GSTP1 MF1, GSTP1 MR1, respectively. Each fragment was then cloned into TOPO T/A vector (Invitrogen). Ten colonies of each product were selected for sequencing. To determine the sensitivity of tBGS and conventional BGS in CpG methylation monitoring, we mixed known completely methylated and completely unmethylated DNA templates in different ratios, in 10% increments, for direct sequencing.

RNA-specific Universal Reverse Transcription and PCR:

Total RNA from NHBE and A549 cells was prepared by RNeasy Mini Kit (Qiagen), according to manufacturer's protocol. RT was performed by universal RT primer as previously described (36), avoiding genomic DNA-encoded false positives in the RT-PCR that are yielded by pseudogene-encoded sequences (e.g., GSTP1 and 36B4 processed pseudogene sequences in genomic DNA).

Quantitative RT-PCR was performed in the LightCycler® (Roche, Indianapolis, Ind.) thermocycler using GSTP1 and 36B4 RNA-specific primers (Table 3). RT-PCR target transcript results were normalized to expression levels of the internal reference housekeeping gene 36B4 as previously described (17).

Direct Sequencing of Bisulfite-converted DNA-PCR Products:

Direct sequencing was initially attempted on the bisulfite-modified genomic DNA-derived PCR product for the CYP1B1 promoter. This consistently yielded G background noise for reverse sequencing (FIG. 1) or C background noise for forward sequencing (FIG. 3, bottom).

In FIG. 1, bisulfite genomic DNA was amplified by CYP1B1 promoter-specific, standard-design primers (see Table 1). PCR products were purified and subjected to direct cycle sequencing. The G background for reverse primer sequencing (black tracing) is apparent, and extends beyond the 3' end of the template sequence.

Figure 3:
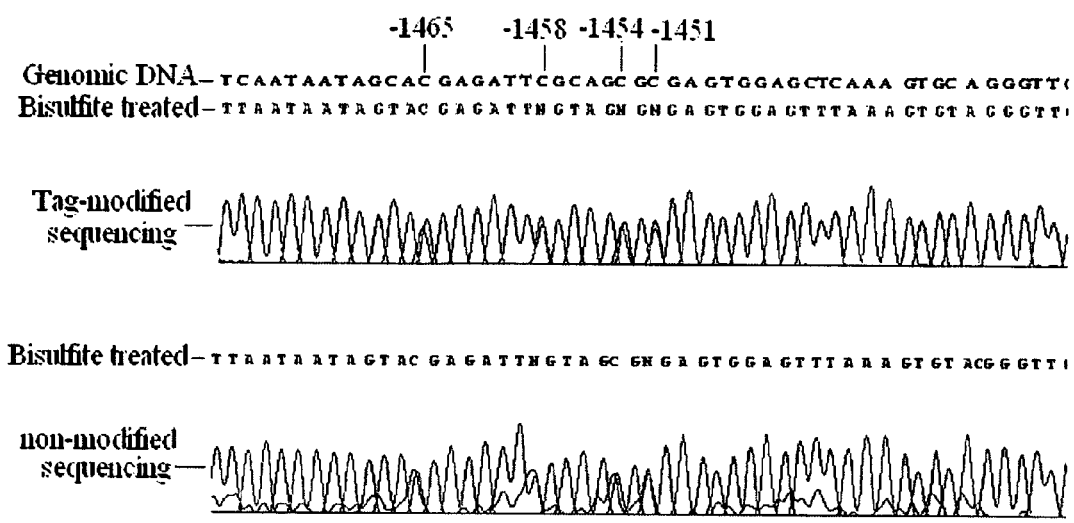
FIG. 3 is a chromatogram tracing of a comparison of tag-modified (top tracing) and tag-unmodified (bottom tracing) PCR product sequencing (SEQ ID NOS 59, 60 & 61, respectively in order of appearance).

FIG. 3 depicts comparison of tag-modified (top tracing) and tag-unmodified (bottom tracing) PCR product sequencing. Bisulfite-converted genomic DNA was amplified by CYP1B1 promoter-specific primers (see Table 1). After GC-tag modification by second-round PCR, the sense strand was sequenced. C background noise was consistently observed in the unmodified PCR product sequencing result, precluding methylation determinations at several positions in this short fragment. The positions refer to the transcription start site of the CYP1B1 gene (U56438). Positions −1458 and −1454 can be seen to be hemi-methylated: one allele is methylated, while the other is not, at each of the two sites.

The background noise, which invariably corresponded to C or G signal, extended beyond the 3' end of the template, presumably from unused ddCTP or ddGTP in the sequencing reaction mixture, or possibly an alteration of gain by the sequencing instrument. Similar results were also observed for other sequence, including the GSTP1 promoter. This phenomenon made it difficult to unambiguously distinguish the partially-methylated CpG site from the unmethylated site, thus rendering direct-to-cycle sequencing interpretation of bisulfite-modified DNA-PCR products unreliable. This background phenomenon can also be found in publications [37, 38] when unmethylated CpG islands are examined.

Since the background C occurred in samples where the majority or all of the C's had been eliminated by bisulfite treatment, reintroduction of true C (or G) would restore appropriate signals for the C lane and thereby reduce background for this channel. GC tag primers were constructed which would include C (and G) in primer design assuring that each base was represented in all PCR products prior to sequencing.

Effect of GC Tag Modification on Direct Sequencing of the PCR Product:

First-round PCR products were subjected to second-round PCR using tag-modified primers containing high C- or G-content tags added to the 5' or 3'end (Table 2). Tag sequences were then used as sequencing primers, as described in the Methods. Upon sequencing, a significant improvement in the clarity of chromatogram tracings was found (FIG. 3); partially-methylated sequences (read as C/T) were clearly distinguishable from unmethylated sites (read as T's in the sequencing reaction). Approximately 5% or more of C and G, respectively, integrated into both strands of the PCR product was sufficient to permit direct cycle sequencing of the PCR product, without cloning. The sensitivity of the tBGS sequencing trace to methylated molecules was approximately 10% (FIG. 4).

Figure 4:
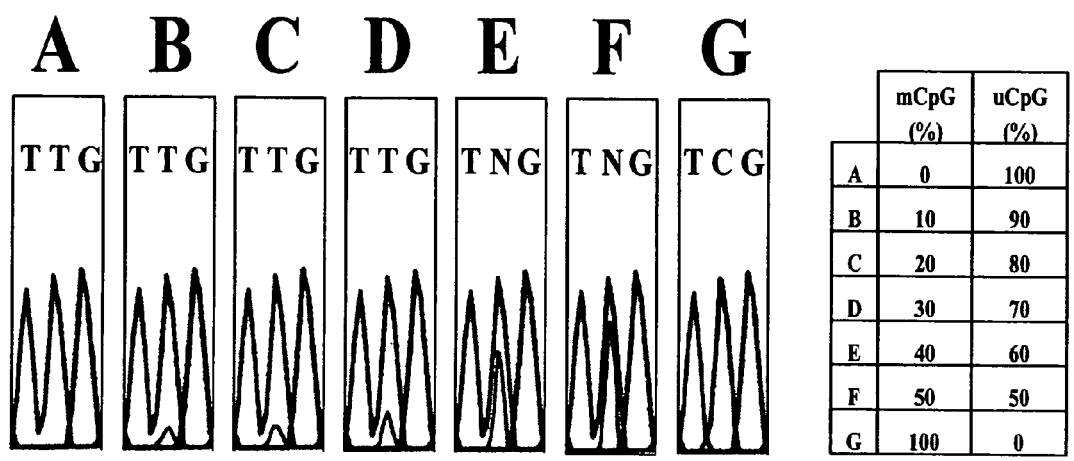
FIG. 4 is a schematic depicting tagged bisulfite genomic sequencing (tBGS) sensitivity to $^m$CpG detection.

FIG. 4 depicts tagged bisulfite genomic sequencing (tBGS) sensitivity to $^m$CpG detection. Bisulfite treatment was performed on NHBE and A549 genomic DNA, where completely methylated or completely unmethylated genomic DNA for the most 5' GSTP1 promoter fragment as assessed by prior conventional (cloning) BGS studies was available. The respective fragments were then PCR-amplified and then inserted in a TA vector. The methylated and unmethylated clones that were verified by sequencing were then mixed together in 10% increments, and subject to direct sequencing. Representative CpG site sequences are displayed from A to G. A: Known unmethylated CpG (uCpG) site from NHBE cells; G: Known methylated CpG (mCpG) site from A549 cell line. The method appeared capable of detecting 10% methylation, similar to the limits of detection for most direct-cycle sequencing techniques, and qualitatively increased with increasing levels of methylation.

Verification of tBGS by Conventional BGS:

For GSTP1, the tBGS methylation results were identical to conventional (cloning) BGS results (FIG. 4). No variation (homo-methylation) in the GSTP1 methylation strand haplotypes was observed by conventional BGS, and none suggested by the tBGS sequence tracings.

Figure 5:
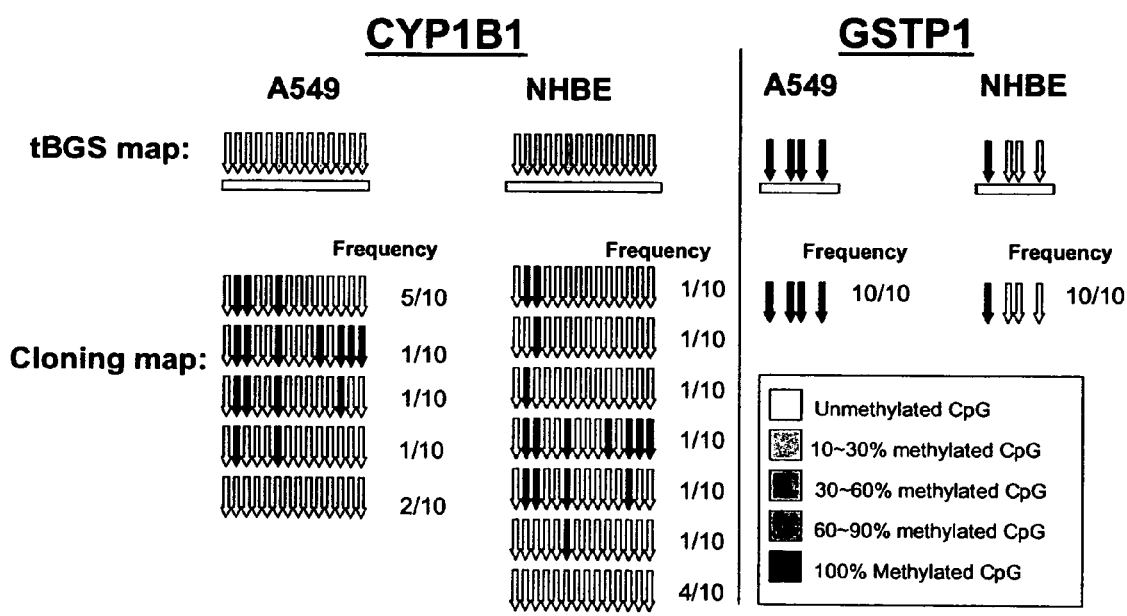
FIG. 5 is a schematic depicting qualitative comparisons of results from tBGS and conventional BGS.

Significant heterogeneity in methylation status in the CYP1B1 haplotypes across DNA strands was detected by conventional BGS for both cell types. This implied that tBGS results reflected a pool of different methylation haplotypes, as expected (FIG. 5). Using conventional BGS as the reference method, tBGS sequence tracings of loci that showed some degree of methylation were called qualitatively positive. That positive signal was then graded according to tracing ratios (height of the unmethylated versus methylated tracing, in quintiles); FIG. 5 depicts this gradation of fraction methylated for tBGS as shades of gray. The degree of methylation ascertained by tBGS sequence chromatogram tracing height ratio was proportional to that fraction of cloned DNA molecules that were methylated (R=0.935, p=0.002), with the tBGS method generally estimating the fraction methylated to be 20-30% higher than that observed in the ten conventionally-sequenced clones (FIG. 5).

FIG. 5 depicts qualitative comparison of results from tBGS and conventional BGS. Genomic DNA was prepared from A549 and NHBE cells. Genomic DNA was bisulfite converted as described, and (a): the CYP1B1 promoter was amplified by 1B1MF1B, 1B1MR4. PCR product was sequenced by tBGS strategy and the conventional (cloning) BGS method. Ten colonies were sequenced for the latter method. (b): GSTP1 promoter was amplified by GSTP1 MF1, GSTP1 MR1 and analyzed in similar parallel fashion using the two methods. The results suggest consistency of methylation map (CpG site) patterns across the two methods, with the pool of DNA molecules analyzed by the tBGS method displaying results consistent with the single DNA molecules analyzed by conventional (cloning) BGS. Shades of gray (CYP1B1 promoter) represent partial methylation, representative of the pool of differently methylated genomic DNA molecules at each CpG site, analyzed by the tBGS method. The GSTP1 promoter showed no partial methylation by either technique.

Figure 6:
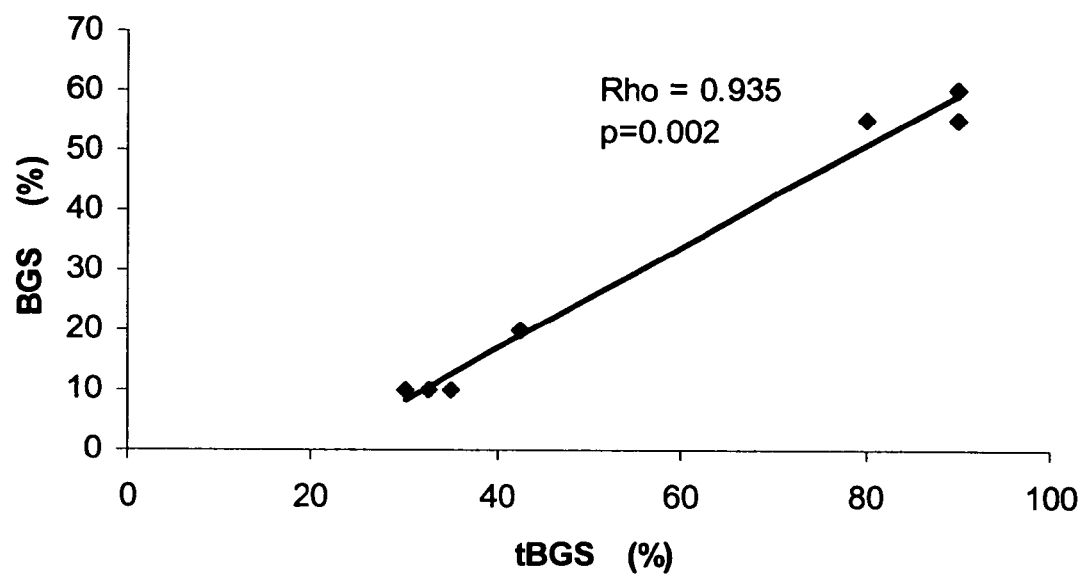
FIG. 6 is a graph depicting the correlations of results from tBGS and conventional BGS.

No false positive methylation calls were made by tBGS; areas free of methylation by tBGS were free of methylation when assayed by conventional BGS. The assessment of sensitivity of tBGS in CpG methylation monitoring, by mixing different ratios of methylated and unmethylated DNA templates in 10% increments, suggested tBGS could routinely detect methylated CpG when present as approximately 10% of the total (FIG. 6). The method routinely yielded clean baseline tracings, enabling this estimation of sensitivity.

FIG. 6 depicts correlations of results from tBGS and conventional BGS. The −1589~−1149 region of CYP1B1 promoter in NHBE and A549 was analyzed by both tBGS and conventional (cloning) BGS. The individual values of methylation degree were assessed by the relative height of the C versus C+T tracings (or in the antisense direction, G/G+A) at each individual CpG site in the region (−1537, −1535, −1518, −1465, −1458, −1454, −1452) by tBGS. The fraction methylated in conventional BGS was performed by assessing the invariably monomorphic tracing yielded by single DNA molecule cloning, and summing the result at each site with the other clones (n=10 clones total). The paired results [e.g. tBGS (50% methylated) versus conventional BGS (3/10 or 30% methylated)] were correlated at each of the seven sites by the non-parametric Spearman correlation test, yielding Rho=0.935, p=0.002.

Methylation Mapping of the Promoter of CYP1B1 and GSTP1:

Screening was performed on an approximately 1.5-kb region of the promoter of the human CYP1B1 gene, and a 1.8-kb region of the promoter of the GSTP1 gene, inclusive of the vast majority of CpG sites in the respective 5'-flanking regions for these two genes. Among the various tissues surveyed from the donors, the methylation patterns in the promoters of CYP1B1 and GSTP1 were completely conserved, being consistent across all tissues and individuals (Table 4). However, in the CYP1B1 promoter, all detected methylation represented partial methylation, ascertained according to second peaks in the sequencing trace at any site. The degree of methylation of CpG sites at −1465, −1458, −1454, −1452, was about 20-30% in all tissues and NHBE cells, versus about 40-50% in A549 cells. CpG sites at −1537, −1535, −1518 were about 80-90% methylated, and at -579 about 40-50%methylated in all tissues and cultured cells [FIG. 7].

Figure 7:
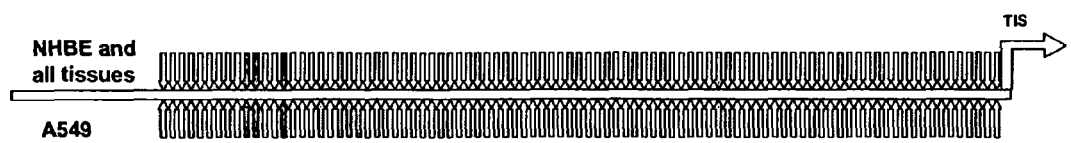
FIG. 7 is a schematic depicting CYP1B1 and GSTP1 promoter methylation maps of malignant A549 lung cells (and other tissues examine), compared with normal human bronchial NHBE cells.
Figure 7:
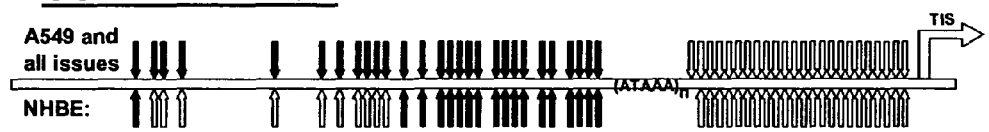

Methylation Pattern and Expression of CYP1B1 and GSTP1 in NHBE and A549 Cells:

The methylation patterns of the CYP1B1 and GSTP1 promoters in cultured NHBE and A549 cells were examined. For both cell lines, the GSTP1 promoter was methylated only in the region 5' to a pentanucleotide repeat. In NHBE cells, the GSTP1 promoter was unmethylated at a 10-CpG site area in the 5' upstream region of the promoter (−1695 to −988); in contrast, this site was completely methylated in A549 cells (FIG. 7). Both findings were confirmed by direct standard BGS employing DNA cloning. No such methylation differences between the cell lines were found in the CYP1B1 promoter; the CYP1B1 promoter in A549 and NHBE showed the same methylation pattern as that observed in all tissue samples (Table 3).

Figure 8:
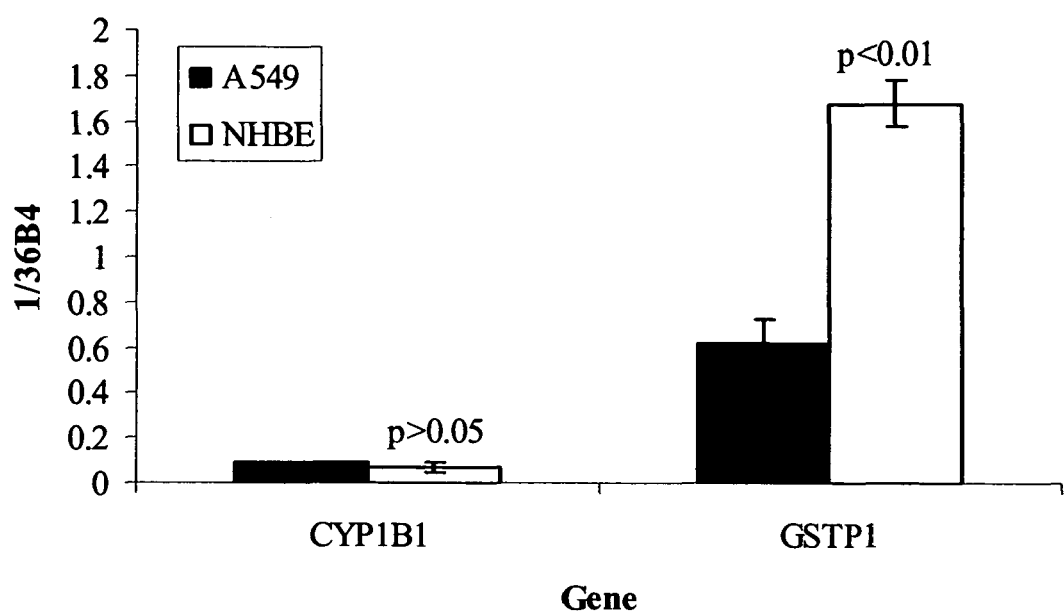
FIG. 8 is a diagram depicting mRNA expression of CYP1B1 and GSTP1 in NHBE and A549 cells.

To assay the functional correlates of the methylation difference in the GSTP1 promoter between NHBE and A549 cells, levels of mRNA transcript encoded by the respective genes were determined, employing RNA-specific real-time quantitative RT-PCR. No difference on CYP1B1 mRNA expression was observed between the two cell lines (FIG. 8). However, GSTP1 mRNA expression was 2.7 times higher in the less-highly methylated NHBE cells than in A549 cells (FIG. 8). This region has not previously been examined for methylation-associated changes in GSTP1 expression.

FIG. 8 depicts mRNA expression of CYP1B1 and GSTP1 in NHBE and A549 cells. The RNA-specific RT-PCR revealed GSTP1 transcript in NHBE cells to be 2.7-fold that in A549 cells. This difference was not observed for CYP1B1 expression levels, where there were no methylation map differences between the two cell types. Target transcript levels (CYP1B1 or GSTP1 ) are scaled to the internal reference housekeeper 36B4 (1/36B4). Data are shown as mean value ±SD (n=3).

Figure 9:
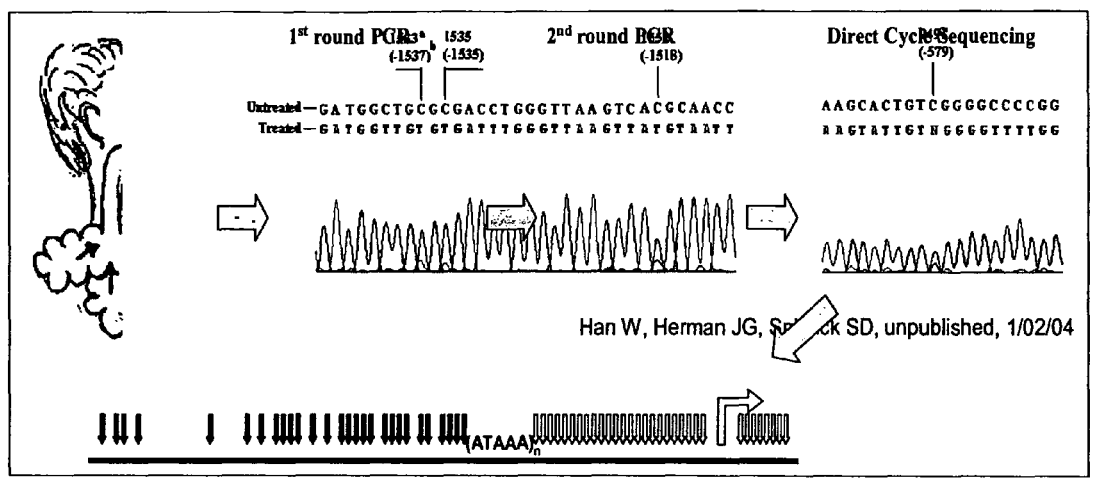
FIG. 9 is a schematic drawing of GSTP1 promoter PCR amplification from exhaled breath condensate (EBC) from one healthy donor screened with the tBGS technique(SEQ ID NOS 62 & 63, respectively in order of appearance).

FIG. 9 depicts GSTP1 promoter PCR amplification from exhaled breath condensate (EBC) from one healthy donor was screened with the new tBGS technique. EBC was collected at three separate time-points separated by months from the same subject with identical results. Genomic DNA isolation, bisulfite conversion, GSTP1 promoter amplification in two steps (corresponding to the two gels), and direct cycle sequencing was performed using the t-BGS approach. In the instance of GSTP1 , six separate PCR amplifications (corresponding to each lane) were needed to cover the CpG sites from −1828 to +56, with the transcription start site as the reference. The first round-PCR allows amplification of bisulfite-treated DNA. The second round-PCR is performed with the tagged-primers, permitting subsequent direct sequencing. Transcription start site is marked with a right-angle arrow.

In order to analyze the CpG methylation patterns in human carcinogenesis, it is imperative to have available a simplified, higher-throughput analysis technique for surveying regions of interest (19; 27; 39-41). Several methods have been devised for CpG methylation detection (19), but the most comprehensive approach to surveying large regions of DNA methylation at high resolution remains genomic sequencing (42, 43). Traditionally, this technique has required cloning of the PCR product into a vector for successful sequencing (31, 41) in multiple clones (generally≧5-10), making it technically difficult and labor-intensive, and unsuited for high-throughput investigations. This invention relates to a simplified method, tBGS, which permits higher-throughput genomic DNA screening for the construction of methylation maps from non-invasively collected human specimens.

The present invention provides significant advantages over conventional BGS. Among these advantages, tBGS: (1) enables the construction of methylation maps across kilobase-sized regions of DNA, at single-base resolution, while avoiding the need for DNA fragment cloning. This simplification reduces DNA isolation and sequencing 5-10-fold, by circumventing the requirement for evaluation of 5-10 clones per DNA fragment for evaluation by conventional BGS; (2) employs second round tag primers that are easily adapted from first round genomic DNA primers; (3) uses two rounds of PCR, thus rendering it highly sensitive for trace genomic DNA application, as for typical small human specimen use; (4) tag sequences can be used as sequencing reaction primers; (5) has performance and internal control sequence advantages similar to those of conventional BGS; and (6) yields partial methylation results that correlate with those of conventional BGS. Performance in trace DNA sample situations was demonstrated in this report for a variety of tissues, including the demanding applications of exfoliated cells and exhaled breath samples.

The tBGS method has certain limitations. First, like conventional BGS and all other technologies employing conventional Sanger-based cycle sequencing chemistries, tBGS requires that a minimum of ~5-10% of chromosomal DNA be methylated at the site of interest to enable detection by the laser and capillary set up of the sequencing device (e.g., ABI 3100,3700). This is not considered a major limitation, as the rarely methylated site (<5%) is unlikely to have major functional effects on the whole population of cells from which the DNA molecules are extracted. Where greater sensitivity is needed, biased PCR approaches, such as MSP, may be required. Second, localization of a specific methylated site to a particular DNA strand (or "allele") for construction of the methylation equivalent of haplotype, is not possible without cloning, since the current tBGS technique pools all template DNA molecules for sequencing (as is true in general of PCR product sequencing techniques, and MSP as well). Third, the tBGS method is not quantitative, as currently implemented, for determination of the exact percent of chromosomes methylated at any one CpG site; adaptations to render it semi-quantitative can be envisioned, as piloted in this study, by measuring C/C+T peak height. Fourth, the method currently requires a two-step PCR amplification of the bisulfite-treated genomic DNA. While initial attempts have suggested the feasibility of reducing this to one round of PCR, using the original-design tagged primers (not shown), more development is required. It should be noted, however, that a disadvantage to the one-step approach relative to the two-step amplification is that less final PCR product is generated in the one-step. In that case, more of the original, potentially precious human extract may be required to execute broad genomic methylation surveys.

This tBGS method is therefore useful in higher-throughput promoter methylation mapping from clinical samples to find potentially disease-related CpG methylation sites. tBGS can be used to survey larger regions of pooled DNA, and follow up sites of interest with real-time quantitative MSP (28, 29, 39-41) or other methods, where precise quantitation and sensitivity are enhanced. Critical areas for experimental research on gene regulation might then be cloned.

To demonstrate the performance and translational utility of the tBGS assay, the examples focus on two commonly studied genes, CYP1B1 and GSTP1. Wide inter-individual variation in the mRNA expression of CYP1B1 has been observed over 1000-fold despite identical exposures (17, 18, 44), and has been hypothesized to be responsible for inter-individual differences in susceptibility to exogenous or endogenous mutagen-induced disease. On examination of the promoter methylation pattern in PBMC and exfoliated buccal cells from 40 individuals [including the majority of the samples displaying the >1000-fold range in expression (17), and 10 paired lung tumor tissues and nontumor tissues, we found that only 8 of 119 CpGs were methylated in the CYP1B1 promoter, in a highly conserved pattern for both CpG site location and degree of methylation at any given site, across individuals and tissues. There was no evidence of contamination to explain this result, as cloning of the first round CYP1B1 promoter PCR product revealed clearly differing patterns for A549 and NHBE cells. This result indicates that promoter methylation cannot easily explain the previously-observed, wide inter-individual differences we have observed in the expression of CYP1B1 mRNA in these same tissue samples (17).

Promoter methylation has been demonstrated to be one of the factors implicated in the regulation of GSTP1 gene expression in a wide range of human tissues (45). A consistent pattern was seen in the GSTP1 promoter methylation pattern in PBMCs and buccal cells from 40 individuals, and 10 lung tumor and nontumor tissues; 30 of 82 CpG sites were completely methylated, the remainders were completely unmethylated, and this uniformly conserved pattern held across all tissue types assayed, and across all individual subjects. This conserved methylation pattern may be important in maintenance of GSTP1 expression levels. This result again indicates that promoter methylation cannot easily explain the previously-observed, wide inter-individual differences we have determined in the expression of GSTP1 in these same normal tissue samples (17). In studies employing MSP techniques in tumors, GSTP1 methylation was noted to be only rarely detected (in the limited region immediately surrounding the transcription start site) in non-small cell lung tumors (25, 46, 47), and virtually never in normal tissues. Consistent with these MSP-based findings, the current tBGS-based studies did not detect methylation in the 3' region of the GSTP1 promoter.

In cell culture, however, the GSTP1 methylation in normal lung (NHBE) cells differed both from that in malignant lung (A549) cells in culture, as well as from that in all the tissue specimens described above, including non-tumor lung tissue. For the NHBE cells uniquely, the region (−1695 to −988) was unmethylated at a block of 10 CpG sites. As a corollary, GSTP1 mRNA expression was 2.7-fold higher in NHBE cells than in A549 cells. Published MSP studies have not explored this region. The degree of 5' promoter methylation is inversely correlated with gene expression levels (28); it suggests that a methylated region, quite remote from the transcription start site, may still modulate levels of gene expression.

The ability to perform methylation mapping from trace amounts (100-250 ng) of genomic DNA in exhaled breath condensate in the one subject studied at multiple time-points, suggests the possibility of non-invasively sampling lung epithelium for "field cancerization".

In summary, the examples demonstrate a simplified method for screening the detailed methylation status within large DNA regions has been devised across human tissues and across donors. It holds significant potential for facilitating the study of DNA methylation, in a variety of translational research contexts, including direct human studies in gene regulation and carcinogenesis, biomarker development, and therapeutic efficacy.

TABLES

Table 1. First-round methylation PCR primers for CYP1B1 and GSTP1 promoters

| | Primer | Sequence | Product | Region |
|---|---|---|---|---|
| CYP1B1 | 1B1MF1B | TTT GGAGTG GGATTTGGTGG (SEQ ID NO: 3) | P1 | 1481-1921[a] |
| | 1B1MR4 | ACTCTATAATCTTCCTAAAC (SEQ ID NO: 4) | | (−1589~−1149)[b] |
| | 1B1MF2 | GTTTAGGAAGATTATAGAGT (SEQ ID NO: 5) | P2 | 1902-2529 |
| | 1B1MR2ab | AATCCCTAAAAATAACC(A/G)CTCC (SEQ ID NO: 6) | | (−1168~−541) |
| | 1B1MF3 | TTTGTGTGTTTAAGTATTGT(T/C)G (SEQ ID NO: 7) | P3 | 2471-2819 |
| | 1B1MR5 | AACCACCTCCAATCAAAAC (SEQ ID NO: 8) | | (−599~−251) |
| | 1B1MF4 | G(C/T)GGAGAGGGAAGGGAGGT (SEQ ID NO: 9) | P4 | 2696-3090 |
| | 1B1MR3ab | CACAACTAAAATC(A/G)CAAAA (SEQ ID NO: 10) | | (−374~+20) |
| GSTP1 | GSTP1MF1 | ATATTTAGGGAAAATAGGAAAGGATTTA (SEQ ID NO: 11) | P5 | 30-333 |
| | GSTP1MR1 | CACAAACAAAAAAACAACAAACACTATA (SEQ ID NO: 12) | | (−1856~−1553) |
| | GSTP1MF2 | TTTAAGGTATAGTTATTAAAAGGAA (SEQ ID NO: 13) | P6 | 729-1136 |
| | GSTP1MR2 | TCCCAAAATACTAAAATTACAAAC (SEQ ID NO: 14) | | (−1158~−751) |
| | GSTP1MF3 | TTTAGAATTTTAAATAAAAGTTGGA (SEQ ID NO: 15) | P7 | 1067-1353 |

TABLES-continued

Table 1. First-round methylation PCR primers for CYP1B1 and GSTP1 promoters

| Primer | Sequence | Product | Region |
|---|---|---|---|
| GSTP1MR3 | ATAACCCAAACTAAAATACAATAAC (SEQ ID NO: 16) | | (-820~-534) |
| GSTP1MF4 | GGTTGAAGTAGAATTGTTTGAATT(C/T)G (SEQ ID NO: 17) | P8 | 1269-1506 |
| GSTP1MR4 | TAAAAACCACTTAAAAAAAAAAAATTAC (SEQ ID NO: 18) | | (-618~-381) |
| GSTP1MF5 | GTAATTTTTTTTTTTTAAG(C/T)TGGTTTTTA (SEQ ID NO: 19) | P9 | 1478-1683 |
| GSTP1MR5 | CCTTTCCCTCTTTCCCAAAT (SEQ ID NO: 20) | | (-409~-204) |
| GSTP1MF6 | TTGTTGTTTGTTTATTTTTTAGGTTT (SEQ ID NO: 21) | P10 | 1630-1966 |
| GSTP1MR6 | ACTAAAAACTCTAAACCCCATCCC (SEQ ID NO: 22) | | (-257~+80) |

All primers are 5'→3' oriented; [a] positions referred to GenBank sequence (U56438 for CYP1B1 and AY324387 for GSTP1); [b] position refers to transcription initiation site.

All primers are 5'→3' oriented; [a] positions referred to GenBank sequence (U56438 for CYP1B1 and AY324387 for GSTP1); [b] positions refers to transcription initiation site.

TABLE 2

Second-round PCR primers for CYP1B1 and GSTP1 promoters

| Template | Primer | Sequence | Region |
|---|---|---|---|
| P1 | CF1 | CCACTCACTCACCCACCCTTTGGAGTGGGATTT (SEQ ID NO: 23) | 1481-1718 |
| | MR1718 | GGGTGGGAGGTGGGAGGGATATCTAATTAACCAAA (SEQ ID NO: 24) | (-1589~-1352) |
| P1 | MF1677 | CCACTCACTCACCCACCCTTTGATGAAGTTAGTAT (SEQ ID NO: 25) | 1677-1921 |
| | GR1 | GGGTGGGAGGTGGGAGGGACTCTATAATCTTCC (SEQ ID NO: 26) | (-1393~-1149) |
| P2 | CF2 | CCACTCACTCACCCACCCGTTTAGGAAGATTAT (SEQ ID NO: 27) | 1902-2327 |
| | MR2327 | GGGTGGGAGGTGGGAGGGAACCTAAAAAAACTAAC (SEQ ID NO: 28) | (-1168~-743) |
| P2 | MF2151 | CCACTCACTCACCCACCCAGGGATATGATTGGAGT (SEQ ID NO: 29) | 2151-2529 |
| | GR2 | GGGTGGGAGGTGGGAGGGAATCCCTAAAAATAA (SEQ ID NO: 30) | (-919~-541) |
| P3 | CF3 | CCACTCACTCACCCACCCTTTGTGTGTTTAAGT (SEQ ID NO: 31) | 2471-2819 |

TABLE 2-continued

Second-round PCR primers for CYP1B1 and GSTP1 promoters

| Template | Primer | Sequence | Region |
|---|---|---|---|
| | GR3 | GGGTGGGAGGTGGGAGGGAACCACCTCCAA TCA (SEQ ID NO: 32) | (−599~−251) |
| P4 | CF4 | CCACTCACTCACCCACCCGC/TGGAGAGGGA AGGG (SEQ ID NO: 33) | 2696-2885 |
| | MR2885 | GGGTGGGAGGTGGGAGGGACCAACAAACTT TCATAA (SEQ ID NO: 34) | (−374~−185) |
| P4 | MF2801 | CCACTCACTCACCCACCCGTTTTGATTGGAGG TGGT (SEQ ID NO: 35) | 2801-3090 |
| | GR4 | GGGTGGGAGGTGGGAGGGCACAACTAAAAT CA/GC (SEQ ID NO: 36) | (−269~+20) |
| P5 | GSTP1MFT1 | CCACTCACTCACCCACCCTAGGAAAGGATTT A (SEQ ID NO: 37) | 44-319 |
| | GSTP1MRT1 | GGGTGGGAGGTGGGAGGGCAACAAACACTA TA (SEQ ID NO: 38) | (−1842~−1539) |
| P6 | GSTP1MFT2 | CCACTCACTCACCCACCCGTTATTAAAAGGA A (SEQ ID NO: 39) | 739-1126 |
| | GSTP1MRT2 | GGGTGGGAGGTGGGAGGGCTAAAATTACAA AC (SEQ ID NO: 40) | (−1147~−741) |
| P7 | GSTP1MFT3 | CCACTCACTCACCCACCCAAATAAAAGTTGG A (SEQ ID NO: 41) | 1078-1342 |
| | GSTP1MRT3 | GGGTGGGAGGTGGGAGGGTAAAATACAATA AC (SEQ ID NO: 42) | (−809~−523) |
| P8 | GSTP1MFT4 | CCACTCACTCACCCACCCATTGTTTGAATT(C/ T)G (SEQ ID NO: 43) | 1281-1491 |
| | GSTP1MRT4 | GGGTGGGAGGTGGGAGGGAAAAAAAAAATTAC (SEQ ID NO: 44) | (−606~−366) |
| P9 | GSTP1MFT5 | CCACTCACTCACCCACCCTTAAG(C/T)GGTTT TTA (SEQ ID NO: 45) | 1493-1677 |
| | GSTP1MRT5 | GGGTGGGAGGTGGGAGGGCCTCTTTCCCAAAT (SEQ ID NO: 46) | (−394~−198) |
| P10 | GSTP1MFT6 | CCACTCACTCACCCACCCTATTTTTTAGGTTT (SEQ ID NO: 47) | 1642-1956 |
| | GSTP1MRT6 | GGGTGGGAGGTGGGAGGGCTAAACCCCATCCC (SEQ ID NO: 48) | (−245~+70) |

All primers are 5'→3' oriented; bold letters indicate tag sequence.

TABLE 3

Primers for quantitative RT-PCR

| | | Primer Sequence |
|---|---|---|
| RT | URT | 5'-AAC GAG ACG ACG ACA GAC TTT TTT TTT TTT TTT TTT A/C/G A/C/G A/C/G/T-3' (SEQ ID NO: 49) |
| CYP1B1 | DSF | 5'-GCC ACT ATC ACT GAC ATC T-3' (SEQ ID NO: 50) |
| | DSR | 5'-CTT GCC TCT TGC TTC TTA TT-3' (SEQ ID NO: 51) |
| GSTP1 | UF2 | 5'-TCT CCT TCG CTG ACT ACA AC-3' (SEQ ID NO: 52) |
| | UR | 5'-AAC GAG ACG ACG ACA GAC-3' (SEQ ID NO: 53) |
| 36B4 | UF1 | 5'-GAC AAT GGC AGC ATC TAC AA-3' (SEQ ID NO: 54) |
| | UR | 5'-AAC GAG ACG ACG ACA GAC-3' (SEQ ID NO: 55) |

TABLE 4

Methylated CpG site in the promoters of CYP1B1 and GSTP1

| Gene name | Number of CpG sites examined | Number of CpG sites methylated | Position of methylated CpG |
|---|---|---|---|
| CYP1B1 | 119 | 8 | −579, −1452, −1454, −1458, −1465, −1518, −1535, −1537 |
| GSTP1 | 82 | 30 | −521, −531, −559, −561, −567, −570, −587, −623, −645, −684, −704, −715, −742, −747, −775, −787, −795, −863, −960, −988, −991, −1046, −1052, −1091, −1133, −1315, −1644, −1687, −1695, −1800 |

The data derive from both peripheral blood lymphocytes and exfoliated buccal cells from 40 individuals; from paired nonmalignant and malignant lung tissue specimens from 10 individuals; and from replicate exhaled breath condensate specimens from one individual. No inter-tissue or inter-individual variation in promoter methylation was apparent, for the two gene promoters studied. Positions refer to the respective transcription initiation site (GenBank: U56438 for CYP1B1, and AY324387 for GSTP1).

REFERENCES

1. D. Takai, P. A, Jones. Comprehensive analysis of CpG islands in human chromosomes 21 and 22. Proc. Natl. Acad. Sci. USA 99 (2002) 3740-3745.
2. A. Bird. The Essentials of DNA Methylation. Cell 70 (1992) 5-8.
3. E. Li, C. Beard, R. Jaenisch. Role for DNA Methylation in Genomic Imprinting. Nature 366 (1993) 362-365.
4. K. D. Tremblay, J. R. Saam, R. S. Ingram, S. M. Tilghman, M. S. Bartolomei. A Paternal-Specific Methylation Imprint Marks the Alleles of the Mouse H 19 Gene. Nature Genetics 9 (1995) 407-413.
5. A. D. Riggs, G. P. Pfeifer. X-Chromosome Inactivation and Cell Memory. Trends in Genetics 8 (1992) 169-174.
6. P. A. Jones, P. W. Laird. Cancer epigenetics comes of age. Nature Genetics 21(1999) 163-167.
7. P. Adorjan, J. Distler, E. Lipscher, F. Model, J. Muller, C. Pelet, A. Braun, A. R. Florl, D. Gutig, G. Grabs, A. Howe, M. Kursar, R. Lesche, E. Leu, A. Lewin, S. Maier, V. Muller, T. Otto, C. Scholz, W. A. Schulz, H. H. Seifert, I. Schwope, H. Ziebarth, K. Berlin, C. Piepenbrock, A. Olek. Tumour class prediction and discovery by microarray-based DNA methylation analysis. Nucleic Acids Research 30 (2002) e21.
8. J. F. Costello, M. C. Fruhwald, D. J. Smiraglia, L. J. Rush, G. P. Robertson, X. Gao, F. A. Wright, J. D. Feramisco, P. Peltomaki, J. C. Lang, D. E. Schuller, L. Yu, C. D. Bloomfield, M. A. Caligiuri, A. Yates, R. Nishikawa, H. Su Huang, N. J. Petrelli, X. Zhang, M. S. O'Dorisio, W. A. Held, W. K. Cavenee, C. Plass. Aberrant CpG-island methylation has non-random and tumour-type-specific patterns. Nature Genetics 24 (2000) 132-138.
9. M. Esteller, P. G. Corn, S. B. Baylin, J. G. Herman. A gene hypermethylation profile of human cancer. Cancer Research 61 (2001) 3225-3229.
10. E. Aklillu, M. Oscarson, M. Hidestrand, B. Leidvik, C. Otter, M. Ingelman-Sundberg. Functional analysis of six different polymorphic CYP1B1 enzyme variants found in an Ethiopian population. Molecular Pharmacology 61 (2002) 586-594.
11. J. Lai, D. Vesprini, W. Chu, H. Jernstrom, S. A. Narod. CYP gene polymorphisms and early menarche. Molecular Genetics and Metabolism 74 (2001) 449-457.
12. A. S. Wenzlaff, M. L. Cote, C. H. Bock, S. J. Land, A. G. Schwartz. GSTM1, GSTT1 and GSTP1 polymorphisms, environmental tobacco smoke exposure and risk of lung cancer among never smokers: a population-based study. Carcinogenesis 26 (2005) 395-401.
13. S. Hohaus, A. Di Ruscio, A. Di Febo, G. Massini, F. D'Alo', F. Guidi, G. Mansueto, M. T. Voso, G. Leone. Glutathione S-transferase P1 genotype and prognosis in Hodgkin's lymphoma. Clinical Cancer Research 11 (2005) 2175-2179.
14. J. D. Hayes, D. J. Pulford. The glutathione S-Transferase supergene family: Regulation of GST and the contribution of the isoenzymes to cancer chemoprotection and drug resistance. Critical Reviews in Biochemistry and Molecular Biology 30(1995) 445-600.
15. X. Hu, H. Xia, S. K. Srivastava, C. Herzog, Y. C. Awasthi, X. Ji, P. Zimniak, S. V. Singh. Activity of four allelic forms of glutathione S-transferase hGSTP1-1 for diol epoxides of polycyclic aromatic hydrocarbons. Biochemical and Biophysical Research Communications 238 (1997) 397-402.

16. S. D. Spivack, G. J. Hurteau, M. J. Fasco, L. S. Kaminsky. Phase I and II carcinogen metabolism gene expression in human lung tissue and tumors. Clinical Cancer Research 9 (2003) 6002-6011.
17. S. D. Spivack, G. J. Hurteau, R. Jain, S. V. Kumar, K. M. Aldous, J. F. Gierthy, L. S. Kaminsky. Gene-environment interaction signatures by quantitative mRNA profiling in exfoliated buccal mucosal cells. Cancer Research 64 (2004) 6805-6813.
18. J. C. Willey, E. L. Coy, M. W. Frampton, A. Torres, M. J. Apostolakos, G. Hoehn, W. H. Schuermann, W. G. Thilly, D. E. Olson, J. R. Hammersley, C. L. Crespi, M. J. Utell. Quantitative RT-PCR measurement of cytochromes p450 1A1, 1 B1, and 2B7, microsomal epoxide hydrolase, and NADPH oxidoreductase expression in lung cells of smokers and nonsmokers. American Journal of Respiratory Cell and Molecular Biology 17 (1997) 114-124.
19. O. El Maarri. Methods: DNA methylation. Adv Exp Med Biol. 544 (2003) 197-204.
20. M. F. Fraga, M. Esteller. DNA methylation: a profile of methods and applications. Biotechniques. 33 (2002) 636-649.
21. D. Zhou, W. Qiao, L. Yang, Z. Lu. Bisulfite-modified target DNA array for aberrant methylation analysis. Anal Biochem. 351 (2006) 26-35.
22. J-M. Dupont, J. Tost, H. Jammes, I. G. Git. De novo quantitative bisulfite sequencing using pyrosequencing technology. Anal. Biochem. 333 (2004): 199-127.
23. Tost J, Schatz P, Schuster M, Berlin K, Gut I G. Analysis and accurate quantification of CpG methylation by MALDI mass spectrometry. NAR 2003 31 (9):e50.
24. J. G Herman, J. R. Graff, S. Myohanen, B. D. Nelkin, S. B. Baylin. Methylation-specific PCR: A novel PCR assay for methylation status of CpG islands. Proc. Natl. Acad. Sci. USA 93 (1996) 9821-9826.
25. S. V. Harden, Y. Tokumaru, W. H. Westra, S. Goodman, S. A. Ahrendt, S. C. Yang, D. Sidransky. Gene promoter hypermethylation in tumors and lymph nodes of stage I lung cancer patients. Clinical Cancer Research 9 (2003) 1370-1375.
26. S. E. Cottrell, J. Distler, N. S. Goodman, S. H. Mooney, A. Kluth, A. Olek, I. Schwope, R. Tetzner, H. Ziebarth, K. Berlin. A real-time PCR assay for DNA-methylatiion using methylation-specific blockers. Nucleic Acids Research 32 (2004) e10.
27. O. Topaloglu, M. O. Hoque, Y. Tokumaru, J. Lee, E. Ratovitski, D. Sidransky, C. S. Moon. Detection of promoter hypermethylation of multiple genes in the tumor and bronchoalveolar lavage of patients with lung cancer. Clinical Cancer Research 10 (2004) 2284-2288.
28. C. Jeronimo, R. Henrique, M. O. Hoque, E. Mambo, F. R. Ribeiro, G. Varzim, J. Oliveira, M. R Teixeira, C. Lopes, D. Sidransky. A quantitative promoter methylation profile of prostate cancer. Clinical Cancer Research 10 (2004) 8472-8478.
29. M. J. Fackler, M. McVeigh, J. Mehrotra, M. A. Blum, J. Lange, A. Lapides, E. Garrett, P. Argani, S. Sukumar. Quantitative multiplex methylation-specific PCR assay for the detection of promoter hypermethylation in multiple genes in breast cancer. Cancer Research 64 (2004) 4442-4452.
30. M. Ehrich, M. R. Nelson, P. Stanssens, M. Zabeau, T. Liloglou, G. Xinarianos, C. R. Cantor, J. K. Field, D. van den Boom. Quantitative high-throughput analysis of DNA methylation patterns by base-specific cleavage and mass spectrometry. Proc Natl Acad Sci USA. 102 (2005) 15785-15790.
31. M. Frommer, L. E. McDonald, D. S. Millar, C. M. Collis, F. Watt, G. W. Grigg, P. L. Molloy, C. L. A. Paul. Genomic Sequencing Protocol That Yields A Positive Display of 5-Methylcytosine Residues in Individual DNA Strands. Proc Natl Acad Sci USA. 89 (1992) 1827-1831.
32. R. Feil, J. Charlton, A. P. Bird, J. Walter, W. Reik. Methylation Analysis on Individual Chromosomes—Improved Protocol for Bisulfite Genomic Sequencing. Nucleic Acids Research 22 (1994) 695-696.
33. W. G. Han, B. T. Pentecost, S. D. Spivack. Functional evaluation of novel single nucleotide polymorphisms and haplotypes in the promoter regions of CYP1B1 and CYP1A1 genes. Molecular Carcinogenesis 37 (2003) 158-169.
34. V. K. Rakyan, T. Hildemann, K. L. Novik, J. Lewin, J. Tost, A. V. Cox, T. D. Andrews, K. L. Howe, T. Otto, A. Olek, J. Fischer, I. G. Gut, K. Berlin, S. Beck. DNA methylation profiling of the human major histocompatibility complex: A pilot study for the human epigenome project. PLoS Biology 2 (2004) e405.
35. J. Lewin, A. O. Schmitt, P. Adorjan, T. Hildmann, C. Piepenbrock. Quantitative DNA methylation analysis based on four-dye trace data from direct sequencing of PCR amplificates. Bioinformatics 20 (2004) 3005-3012.
36. G. J. Hurteau, S. D. Spivack. mRNA-specific reverse transcription-polymerase chain reaction from human tissue extracts. Analytical Biochemistry 307 (2002) 304-315.
37. S. Mulero-Navarro, J. M. Carvajal-Gonzalez, M. Herranz, E. Ballestar, M. F. Fraga, S. Ropero, M. Esteller, P. M. Femandez-Salguero. The dioxin receptor is silenced by promoter hypermethylation in human acute lymphoblastic leukemia through inhibition of Sp1 binding. Carcinogenesis. 12 (2006) [Epub ahead of print].
38. U. Deligezer, N. Erten, E. E. Akisik, N. Dalay. Methylation of the INK4A/ARF locus in blood mononuclear cells. Ann Hematol 85 (2006) 102-107.
39. J. T. Attwood, R. L. Yung, B. C. Richardson. DNA methylation and the regulation of gene transcription. Cellular and Molecular Life Sciences 59 (2002) 241-257.
40. M. Ehrlich. Expression of various genes is controlled by DNA methylation during mammalian development. Journal of Cellular Biochemistry 88 (2003) 899-910.
41. S. J. Clark, J. Harrison, C. L. Paul, M. Frommer. High-Sensitivity Mapping of Methylated Cytosines. Nucleic Acids Research 22 (1994) 2990-2997.
42. L. Liu, R. C. Wylie, N. J. Hansen, L. G. Andrews, T. O. Tollefsbol. Profiling DNA methylation by bisulfite genomic sequencing: problems and solutions. Methods Mol Biol. 287 (2004) 169-79.
43. A. Meissner, A. Gnirke, G. W. Bell, B. Ramsahoye, E. S. Lander, R. Jaenisch. Reduced representation bisulfite sequencing for comparative high-resolution DNA methylation analysis. Nucleic Acids Res. 33 (2005) 5868-5877.
44. S. D. Spivack, G. J. Hurteau, A. A. Reilly, K. M. Aldous, X. X. Ding, L. S. Kaminsky. CYP1B1 expression in human lung. Drug Metabolism and Disposition 29 (2001) 916-922.
45. D. S. Millar, C. L. Paul, P. L. Molloy, S. J. Clark. A distinct sequence (ATAAA)(n) separates methylated and unmethylated domains at the 5'-end of the GSTP1 CpG island. Journal of Biological Chemistry 275 (2000) 24893-24899.
46. S. Zochbauer-Muller, K. M. Fong, A. K. Virmani, J. Geradts, A. F. Gazdar, J. D. Minna. Aberrant promoter methylation of multiple genes in non-small cell lung cancers. Cancer Research 61 (2001) 249-255.
47. S. Toyooka, K. O. Toyooka, K. Miyajima, J. L. Reddy, M. Toyota, U. G. Sathyanarayana, A. Padar, M.S. Tockman, S. Lam, N. Shivapurkar, A. F. Gazdar. Epigenetic down-regulation of death-associated protein kinase in lung cancers. Clinical Cancer Research 9 (2003) 3034-3041.
48. Holland et al. Cancer Medicine, Part II Scientific Foundation, Section 1: Cancer Biology.

We claim:

1. A method for determining the degree of methylation of genomic DNA, said method comprising:
   (a) providing a genomic DNA;
   (b) modifying said DNA by bisulfate conversion of cytosine to uracil;
   (c) amplifying said bisulfite-modified DNA by PCR to produce a first PCR product;
   (d) amplifying said first PCR product by PCR using a tag-modified primer to yield a second PCR product comprising a cytosine/guanosine enriched tag, wherein said tag-modified primer comprises a region that is complementary to a target DNA and a tag having a non-complementary nucleotide sequence containing at least 50% cytosine or guanosine;
   (e) purifying said second PCR product;
   (f) sequencing said purified second PCR product comprising the cytosine/guanosine enriched tag to obtain a nucleotide sequence of said second PCR product;
   (g) analyzing the nucleotide sequence obtained from step (f) to determine the degree of methylation of said DNA.

2. The method of claim 1, wherein said sequencing of said purified second PCR product is by direct cycle sequencing.

3. The method of claim 1, wherein said tag-modified primer comprises a 5-50 base tag containing at least 5 cytosines.

4. The method of claim 1, wherein said tag-modified primer comprises a 10-30 base tag containing at least 5 cytosines.

5. The method of claim 1, wherein said tag-modified primer comprises a 18-22 base tag containing at least 5 cytosines.

6. The method of claim 1, wherein said tag-modified primer comprises a 5-50 base tag containing at least 5 guanosines.

7. The method of claim 1, wherein said tag-modified primer comprises a 10-30 base tag containing at least 5 guanosines.

8. The method of claim 1, wherein said tag-modified primer comprises an 18-22 base tag containing at least 5 guanosines.

9. The method of claim 1, wherein two or more pairs of promoter-specific primers are used.

10. A method for identifying an individual at risk for lung cancer comprising:
    (a) providing a DNA sample from said patient;
    (b) modifying said DNA by bisulfite conversion of cytosine to uracil;
    (c) amplifying said bisulfite-modified DNA by PCR using a promoter-specific primer for a gene associated with lung cancer to produce a first PCR product;
    (d) amplifying said first PCR product by PCR using a tag-modified primer to yield a second PCR product comprising a cytosine/guanosine enriched tag, wherein said tag-modified primer comprises a region that is complementary to a promoter of the gene associated with lung cancer and a tag having a non-complementary nucleotide sequence containing at least 50% cytosine or guanosine;
    (e) purifying said second PCR product;
    (f) sequencing said purified second PCR product comprising the cytosine/guanosine enriched tag to obtain a nucleotide sequence of said second PCR product;
    (g) analyzing the nucleotide sequence obtained from step (f) to determine the degree of methylation of said DNA from said patient, wherein a high degree of methylation is indicative of a risk of lung cancer.

11. The method of claim 10, wherein said DNA is collected from an exhaled breathe condensate sample.

12. The method of claim 10, wherein said DNA is collected from a peripheral blood mononuclear cell.

13. The method according to claim 10, wherein said DNA is collected from a buccal cell.

14. The method of claim 10, wherein DNA is amplified using CYP1B1 promoter specific primers.

15. The method of claim 10, wherein DNA is amplified using GSTP1 promoter specific primers.

16. The method of claim 10, wherein said sequencing of said purified second PCR product is by direct cycle sequencing.

17. A method for determining the degree of methylation of genomic DNA, said method comprising:
    (a) providing a genomic DNA;
    (b) modifying said DNA by bisulfite conversion of cytosine to uracil;
    (c) amplifying said bisulfite-modified DNA by PCR using a tag-modified promoter-specific primer for a gene associated with lung cancer to yield a PCR product comprising a cytosine/guanosine enriched tag, wherein said tag-modified primer comprises a region that is complementary to a promoter of the gene associated with lung cancer and a tag having a non-complementary nucleotide sequence containing at least 50% cytosine or guanosine;
    (d) purifying said PCR product;
    (e) sequencing said purified PCR product comprising the cytosine/guanosine enriched tag to obtain a nucleotide sequence of said PCR product;

(f) analyzing the nucleotide sequence obtained from step (e) to determine the degree of methylation of said DNA.

18. A method for identifying an individual at risk for lung cancer comprising:
   (a) providing a DNA sample from said individual;
   (b) modifying said DNA by bisulfite conversion of cytosine to uracil;
   (c) amplifying said bisulfite-modified DNA by PCR using a tag-modified primer to yield a PCR product comprising a cytosine/guanosine enriched tag, wherein said tag-modified primer comprises a region that is complementary to a target DNA and a tag having a noncomplementary nucleotide sequence enriched for cytosine or guanosine;
   (d) purifying said PCR product;
   (e) sequencing said purified PCR product comprising the cytosine/guanosine enriched tag to obtain a nucleotide sequence of said PCR product;
   (f) analyzing the nucleotide sequence obtained from step (e) to determine the degree of methylation of said DNA from said patient, wherein a high degree of methylation is indicative of a risk of lung cancer.

19. A method for determining the degree of methylation of genomic DNA, said method comprising:
   (a) providing a genomic DNA;
   (b) modifying said DNA by bisulfite conversion of cytosine to uracil;
   (c) amplifying said bisulfite-modified DNA by PCR using a tag-modified primer to yield a PCR product comprising a cytosine/guanosine enriched tag, wherein said tag-modified primer comprises a region that is complementary to a target DNA and a tag having a non-complementary nucleotide sequence containing at least 50% cytosine or guanosine at an end of the complementary region;
   (d) purifying said PCR product;
   (e) sequencing said purified PCR product comprising the cytosine/guanosine enriched tag of said PCR product to obtain a nucleotide sequence of said PCR product;
   (f) analyzing the nucleotide sequence obtained from step (e) to determine the degree of methylation of said DNA.

* * * * *

SEQUENCE LISTING

<160> NUMBER OF SEQ ID NOS: 63

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccactcactc acccaccc                                                       18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggtgggagg tgggaggg                                                       18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttggagtgg gatttggtgg                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
actctataat cttcctaaac                                                     20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtttaggaag attatagagt                                                     20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

-continued

```
aatccctaaa aataaccrct cc                                             22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tttgtgtgtt taagtattgt yg                                             22

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaccacctcc aatcaaaac                                                 19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gyggagaggg aagggaggt                                                 19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cacaactaaa atcrcaaaa                                                 19

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atatttaggg aaaataggaa aggattta                                       28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```

```
cacaaacaaa aaaacaacaa acactata                                          28

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tttaaggtat agttattaaa aggaa                                             25

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tcccaaaata ctaaaattac aaac                                              24

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tttagaattt taaataaaag ttgga                                             25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ataacccaaa ctaaaataca ataac                                             25

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggttgaagta gaattgtttg aattyg                                            26

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
taaaaaccac ttaaaaaaaa aaaaattac                                         29
```

```
<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtaatttttt ttttttaag ytggtttta                                          30

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cctttccctc tttcccaaat                                                   20

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttgttgtttg tttatttttt aggttt                                            26

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
actaaaaact ctaaacccca tccc                                              24

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccactcactc acccaccctt tggagtggga ttt                                    33

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gggtgggagg tgggagggat atctaattaa ccaaa                                  35
```

```
<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccactcactc acccacccTT tgatgaagtt agtat                                35

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gggtgggagg tgggagggac tctataatct tcc                                 33

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccactcactc acccacccgt ttaggaagat tat                                 33

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gggtgggagg tgggagggaa cctaaaaaaa ctaac                               35

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccactcactc acccacccag ggatatgatt ggagt                               35

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gggtgggagg tgggagggaa tccctaaaaa taa                                 33
```

```
<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccactcactc acccaccctt tgtgtgttta agt                                33

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gggtgggagg tgggagggaa ccacctccaa tca                                33

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccactcactc acccacccgy ggagagggaa ggg                                33

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gggtgggagg tgggagggac caacaaactt tcataa                             36

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccactcactc acccacccgt tttgattgga ggtggt                             36

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gggtgggagg tgggagggca caactaaaat crc                                33

<210> SEQ ID NO 37
```

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccactcactc acccaccccta ggaaaggatt ta                              32

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gggtgggagg tgggagggca acaaacacta ta                              32

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccactcactc acccacccgt tattaaaagg aa                              32

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gggtgggagg tgggagggct aaaattacaa ac                              32

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ccactcactc acccacccaa ataaaagttg ga                              32

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gggtgggagg tgggagggta aaatacaata ac                              32

<210> SEQ ID NO 43
<211> LENGTH: 32

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccactcactc acccacccat tgtttgaatt yg                                    32

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gggtgggagg tgggagggaa aaaaaaatt ac                                     32

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccactcactc acccaccctt aagctggttt tta                                   33

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gggtgggagg tgggagggcc tctttcccaa at                                    32

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ccactcactc acccacccta tttttttaggt tt                                   32

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gggtgggagg tgggagggct aaaccccatc cc                                    32

<210> SEQ ID NO 49
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (42)
<223> OTHER INFORMATION: n=a,t,c,g, other, or unknown

<400> SEQUENCE: 49
aacgagacga cgacagactt tttttttttt tttttttttv vn                    42

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gccactatca ctgacatct                                              19

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cttgcctctt gcttcttatt                                             20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tctccttcgc tgactacaac                                             20

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aacgagacga cgacagac                                               18

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gacaatggca gcatctacaa                                             20
```

```
<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aacgagacga cgacagac                                                  18

<210> SEQ ID NO 56
<211> LENGTH: 82
<212> TYPE: DNA
<213> ORGANISM: Unknown Organism
<220> FEATURE:
<223> OTHER INFORMATION: Description of Unknown Organism: Unknown
      oligonucleotide
<220> FEATURE:
<221> NAME/KEY: modified_base
<222> LOCATION: (2)
<223> OTHER INFORMATION: n=a,t,c,g, other, or unknown
<220> FEATURE:
<221> NAME/KEY: modified_base
<222> LOCATION: (32)
<223> OTHER INFORMATION: n=a,t,c,g, other, or unknown
<220> FEATURE:
<221> NAME/KEY: modified_base
<222> LOCATION: (37)
<223> OTHER INFORMATION: n=a,t,c,g, other, or unknown
<220> FEATURE:
<221> NAME/KEY: modified_base
<222> LOCATION: (43)
<223> OTHER INFORMATION: n=a,t,c,g, other, or unknown
<220> FEATURE:
<221> NAME/KEY: modified_base
<222> LOCATION: (45)
<223> OTHER INFORMATION: n=a,t,c,g, other, or unknown
<220> FEATURE:
<221> NAME/KEY: modified_base
<222> LOCATION: (67)
<223> OTHER INFORMATION: n=a,t,c,g, other, or unknown
<220> FEATURE:
<221> NAME/KEY: modified_base
<222> LOCATION: (81)
<223> OTHER INFORMATION: n=a,t,c,g, other, or unknown

<400> SEQUENCE: 56
cnaaccaaac ccaaacacgt atcaccacct cnctacncac cancnactct ataatcttcc    60
taaacanggg ggggggggg ng                                              82

<210> SEQ ID NO 57
<211> LENGTH: 18
<212> TYPE: DNA
<213> ORGANISM: Unknown Organism
<220> FEATURE:
<223> OTHER INFORMATION: Description of Unknown Organism: Unknown
      oligonucleotide

<400> SEQUENCE: 57
gatgcgtacc gttcgctc                                                  18

<210> SEQ ID NO 58
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 58
gatgcgtauc gttugutu                                                  18

<210> SEQ ID NO 59
<211> LENGTH: 51
<212> TYPE: DNA
<213> ORGANISM: Unknown Organism
<220> FEATURE:
<223> OTHER INFORMATION: Description of Unknown Organism: Unknown
      oligonucleotide

<400> SEQUENCE: 59
tcaataatag cacgagattc gcagcgcgag tggagctcaa agtgcagggt t             51

<210> SEQ ID NO 60
<211> LENGTH: 51
<212> TYPE: DNA
<213> ORGANISM: Unknown Organism
<220> FEATURE:
<223> OTHER INFORMATION: Description of Unknown Organism: Unknown
      oligonucleotide
<220> FEATURE:
<221> NAME/KEY: modified_base
<222> LOCATION: (20)
<223> OTHER INFORMATION: n=a,t,c,g, other, or unknown
<220> FEATURE:
<221> NAME/KEY: modified_base
<222> LOCATION: (25)
<223> OTHER INFORMATION: n=a,t,c,g, other, or unknown
<220> FEATURE:
<221> NAME/KEY: modified_base
<222> LOCATION: (27)
<223> OTHER INFORMATION: n=a,t,c,g, other, or unknown

<400> SEQUENCE: 60
ttaataatag tacgagattn gtagngngag tggagtttaa agtgtagggt t             51

<210> SEQ ID NO 61
<211> LENGTH: 52
<212> TYPE: DNA
<213> ORGANISM: Unknown Organism
<220> FEATURE:
<223> OTHER INFORMATION: Description of Unknown Organism: Unknown
      oligonucleotide
<220> FEATURE:
<221> NAME/KEY: modified_base
<222> LOCATION: (20)
<223> OTHER INFORMATION: n=a,t,c,g, other, or unknown
<220> FEATURE:
<221> NAME/KEY: modified_base
<222> LOCATION: (27)
<223> OTHER INFORMATION: n=a,t,c,g, other, or unknown

<400> SEQUENCE: 61
ttaataatag tacgagattn gtagcgngag tggagtttaa agtgtacggg tt            52

<210> SEQ ID NO 62
<211> LENGTH: 20
<212> TYPE: DNA
<213> ORGANISM: Unknown Organism
<220> FEATURE:
<223> OTHER INFORMATION: Description of Unknown Organism: Unknown
      oligonucleotide

<400> SEQUENCE: 62
aagcactgtc ggggccccgg                                                20

<210> SEQ ID NO 63
```

```
<211> LENGTH: 20
<212> TYPE: DNA
<213> ORGANISM: Unknown Organism
<220> FEATURE:
<223> OTHER INFORMATION: Description of Unknown Organism: Unknown
      oligonucleotide
<220> FEATURE:
<221> NAME/KEY: modified_base
<222> LOCATION: (10)
<223> OTHER INFORMATION: n=a,t,c,g, other, or unknown

<400> SEQUENCE: 63
aagtattgtn ggggttttgg                                                  20
```